United States Patent
Stopek (10) Patent No.: US 10,339,268 B2
(45) Date of Patent: Jul. 2, 2019

(54) SYSTEM AND METHOD FOR CYTOPATHOLOGICAL AND GENETIC DATA BASED TREATMENT PROTOCOL IDENTIFICATION AND TRACKING

(71) Applicant: COVIDIEN LP, Mansfield, MA (US)

(72) Inventor: Joshua B. Stopek, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 453 days.

(21) Appl. No.: 14/926,383

(22) Filed: Oct. 29, 2015

(65) Prior Publication Data

US 2016/0188836 A1 Jun. 30, 2016

Related U.S. Application Data

(60) Provisional application No. 62/097,690, filed on Dec. 30, 2014, provisional application No. 62/097,697, (Continued)

(51) Int. Cl.
*G06F 19/00* (2018.01)
*A61B 34/20* (2016.01)
(Continued)

(52) U.S. Cl.
CPC ............ *G06F 19/321* (2013.01); *A61B 5/062* (2013.01); *A61B 5/6852* (2013.01); *A61B 10/04* (2013.01);
(Continued)

(58) Field of Classification Search
CPC ............ C12Q 1/6886; C12Q 2600/118; C12Q 1/6883; G06F 19/18; G06F 19/325;
(Continued)

(56) References Cited

U.S. PATENT DOCUMENTS 5,836,877 A 11/1998 Zavislan
6,155,603 A 12/2000 Fox
(Continued)

FOREIGN PATENT DOCUMENTS

WO 98/58338 A2 12/1998

OTHER PUBLICATIONS

International Search Report and Written Opinion from Int'l Appl. No. PCT/US2015/066241 dated Mar. 15, 2016.
(Continued)

*Primary Examiner* — Maroun P Kanaan (57) ABSTRACT

A user interface including a present patient data field, a care team field, a disease identification field, and a plurality of fields presenting data including one or more of imaging data, cytopathological data, genetic information and treatment options for an identified target of the present patient based on a correlation of similarities in data from a plurality of prior patients and the data for the identified target of the present patient. The user interface may further include a diagnosis field and/or a field presenting literature or other information relevant to the diagnosis. Additionally, the user interface may further include a field presenting function data of the present patient. The function data may provide details regarding the health of the present patient or details on the health of the organ in which the target is located.

20 Claims, 6 Drawing Sheets

Related U.S. Application Data filed on Dec. 30, 2014, provisional application No. 62/097,713, filed on Dec. 30, 2014, provisional application No. 62/097,721, filed on Dec. 30, 2014.

(51) Int. Cl.

| | | |
|---|---|---|
| *A61B 10/04* | (2006.01) | |
| *G06F 16/22* | (2019.01) | |
| *G06F 16/51* | (2019.01) | |
| *A61B 5/00* | (2006.01) | |
| *A61B 5/06* | (2006.01) | |
| *A61B 18/14* | (2006.01) | |
| *G16H 40/63* | (2018.01) | |
| *G16H 10/60* | (2018.01) | |
| *G16H 50/70* | (2018.01) | |
| *G16H 50/20* | (2018.01) | |
| *G16H 10/40* | (2018.01) | |
| *A61B 18/00* | (2006.01) | |
| *A61B 18/18* | (2006.01) | |

(52) U.S. Cl.
CPC .......... *A61B 18/1492* (2013.01); *A61B 34/20* (2016.02); *G06F 16/22* (2019.01); *G06F 16/51* (2019.01); *G06F 19/3481* (2013.01); *G16H 10/40* (2018.01); *G16H 10/60* (2018.01); *G16H 40/63* (2018.01); *G16H 50/20* (2018.01); *G16H 50/70* (2018.01); *A61B 2018/00577* (2013.01); *A61B 2018/00982* (2013.01); *A61B 2018/1861* (2013.01); *A61B 2034/2051* (2016.02)

(58) Field of Classification Search
CPC .... G06F 19/30; G06F 17/30864; G06F 19/00; G06F 19/3481; G06F 19/321; G01N 2800/52; G01N 33/574; G16H 50/20; G16H 50/70; G16H 10/60; G16H 10/20; G16H 50/30; G16H 20/10; G16H 10/40; G16H 40/63; G06Q 50/24

See application file for complete search history.

(56) References Cited

U.S. PATENT DOCUMENTS

| | | |
|---|---|---|
| 7,343,030 B2 | 3/2008 | Sawyer |
| 7,831,293 B2 | 11/2010 | Ellis et al. |
| 8,650,017 B2 | 2/2014 | Kirnasovsky et al. |
| 8,655,682 B2 | 2/2014 | Srivastava et al. |
| 8,655,817 B2 | 2/2014 | Hasey et al. |
| 8,788,019 B2 | 7/2014 | Downey et al. |
| 2007/0118399 A1* | 5/2007 | Avinash ................ G06F 19/328 705/2 |
| 2008/0221923 A1 | 9/2008 | Shogan |
| 2009/0048515 A1 | 2/2009 | Suri et al. |
| 2010/0105989 A1 | 4/2010 | Inokuchi et al. |
| 2010/0268222 A1* | 10/2010 | Danek ..................... A61N 1/06 606/41 |
| 2012/0232930 A1 | 9/2012 | Schmidt et al. |
| 2013/0268547 A1 | 10/2013 | Boroczky et al. |
| 2014/0228677 A1 | 8/2014 | Grudem, Jr. et al. |
| 2014/0244283 A1 | 8/2014 | Smith |
| 2014/0314292 A1 | 10/2014 | Kamen et al. |
| 2014/0379366 A1* | 12/2014 | Alloway ................ G06F 19/00 705/2 |
| 2015/0106111 A1 | 4/2015 | Gray |
| 2015/0211077 A1 | 7/2015 | Blelloch et al. |

OTHER PUBLICATIONS

Extended European Search Report issued in Appl. No. 15875976.1 dated Jun. 15, 2018 (5 pages).

\* cited by examiner

|  | PATIENT 1 | PATIENT 2 | PATIENT 3 | PATIENT 4 | ... | PATIENT N |
|---|---|---|---|---|---|---|
| RACE | AFRICAN AMERICAN | CAUCASIAN | HISPANIC | CAUCASIAN |  | CHINESE |
| AGE | 59 | 25 | 35 | 50 |  | 38 |
| SEX | F | M | F | M |  | F |
| IMAGES | 1,2,3 | 1,2 | 1 | 1,2,3,4 |  | 1 |
| PATHWAY PLANS | 1,2 | 1,2 | 0 | 1,2,3 |  | 1 |
| LOCATION | RU | LL | RL | RL,RU,LL |  | RL |
| NUMBER | 2 | 2 | 3 | 12 |  | 3 |
| CYTOLOGY | BENIGN | ADENOCARCINOMA | SQUAMOUS CELL CARCINOMA | LARGE CELL CARCINOMA |  | SMALL CELL LUNG CANCER |
| TUMOR MUTATION/REARRANGEMENT | AKT1 | EGFR | KRAS, EGFR, MET | PTEN, MET |  | BRAF |
| COPD | NO | NO | NO | YES |  | NO |
| CHANGE FROM PRIOR BIOPSY | NO | YES | NO | NO |  | NO |
| STANDARD OF CARE | MONITORING | SURGERY/CHEMO./RADIATION | SURGERY/CHEMO./RADIATION | TARGETED TREATMENTS |  | CHEMO./RADIATION |
| LIFE EXPECTANCY W/O TREATMENT | N/A | 2-3 YEARS | 6 MONTHS | 3-6 MONTHS |  | 1 YEAR |
| TREATMENT | MONITORING | SURGERY | RADIATION | RADIATION AND TARGETED TREATMENTS |  | CHEMO. |
| OUTCOME | STABLE - NO GROWTH | SUCCESSFUL REMOVAL AT 6 MO. | NEW TUMORS AT 6 MONTHS/ PRIOR TREATED TUMORS SUCCESSFULLY TREATED | DECEASED AT 2 MONTHS |  | 1 YEAR NO RELAPSE |

SYSTEM AND METHOD FOR CYTOPATHOLOGICAL AND GENETIC DATA BASED TREATMENT PROTOCOL IDENTIFICATION AND TRACKING

CROSS-REFERENCE TO RELATED APPLICATIONS

This application claims the benefit of and priority to U.S. Provisional Patent Application Nos. 62/097,690, 62/097,697, 62/097,713, and 62/097,721, all of which were filed on Dec. 30, 2014. This application is related to U.S. patent application Ser. Nos. 14/926,335, 14/926,360, and 14/926,528, all of which were filed on Oct. 29, 2015. The entire contents of each of the above applications are hereby incorporated herein by reference.

BACKGROUND

Technical Field

The present disclosure relates to systems and methods for retrieving a biopsy sample, obtaining cytopathological information about the biopsy sample, obtaining genetic information about biopsy sample, identifying a treatment course, performing the treatment, observing the effects of the treatment course on the target from which the biopsy sample was taken, and maintaining an updating a database correlating each of these types of data.

Description of Related Art

A common device for inspecting the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments (e.g., diagnostic instruments such as biopsy tools or therapeutic instruments such as ablation catheters) can be inserted.

Bronchoscopes, however, are limited in how far they may be advanced through the airways due to their size. Where the bronchoscope is too large to reach a target location deep in the lungs a clinician may utilize certain real-time imaging modalities such as fluoroscopy. Fluoroscopic images, while useful present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB), system currently sold by Covidien LP. Such systems are generally referred to as electromagnetic navigation or EMN systems. The details of such a system are described in the commonly assigned U.S. Pat. No. 7,233,820, filed on Mar. 29, 2004 by Gilboa and entitled ENDOSCOPE STRUCTURES AND TECHNIQUES FOR NAVIGATING TO A TARGET IN BRANCHED STRUCTURE, the entire contents of which are incorporated herein by reference.

Regardless of whether using a bronchoscope or an EMN system, upon identification of a tumor, mass, or other area of interest a clinician will generally take a biopsy in order to conduct pathology testing. The result of the pathology will identify whether the tumor or area of interest is cancerous, and will drive the next steps that a clinician will undertake with respect to that patient. The present disclosure is directed to systems and methods to assist the clinician in determining those next steps.

SUMMARY

In an aspect of the present disclosure a user interface is provided. The user interface includes a present patient data field, a care team field, a disease identification field, and a plurality of fields presenting data including one or more of imaging data, cytopathological data, genetic information and treatment options for an identified target of the present patient wherein the treatment options are based on a correlation of similarities in data from a plurality of prior patients and the data for the identified target of the present patient. The user interface may further include a diagnosis field and/or a field presenting literature or other information relevant to the diagnosis. Additionally, the user interface may further include a field presenting function data of the present patient. The function data may provide details regarding the health of the present patient or details on the health of the organ in which the target is located.

The correlation of similarities may be based on cytopathological data stored in the database and the cytopathological data of the present patient. Additionally, or alternatively, the correlation of similarities may be based on the genetic information stored in the database and the genetic information of the present patient. The correlation of similarities may be based on at least one of the imaging, cytopathology, genetic information, sex, race, and age data stored in the database and the corresponding data of the present patient.

Additionally, the presented imaging data of the target, cytopathology of the target, genetic information of the target may be selectable by a user to present further details of each. The presented treatment options may include the standard of care, clinical trials, investigational treatments, and/or combinations thereof. Additionally, or alternatively, the presented treatment options may include an expected outcome based on observed outcomes stored in the database related to the prior biopsy samples used in the correlation. Additionally, or alternatively, the presented treatment options may include treatment details including one or more of power, intensity, dosage, duration, number of cycles, treatment regimen, co-treatments, and timing of each. Additionally, the presented treatment options may be accessible to a care team via a network.

The database may store any or all of the patient data, the image data, the cytological examination results, and the genetic information in a database accessible via a network. In one aspect, upon selecting a treatment option, the selected treatment option is stored in the database. Additionally, or alternatively, upon executing the selected treatment, the treatment details may be stored in the database including one or more of power, intensity, dosage, duration, number of cycles, treatment regimen, co-treatments, and timing of each.

The treatment options presented may be those most commonly undertaken treatments administered to the prior patients having the same cytopathological expression as the present patient. Additionally, or alternatively, the treatment options presented may be those most commonly undertaken treatments administered to the prior patients having the same genetic information as the present patient. Additionally, or alternatively, the presented treatment options may include an expected outcome, the expected outcome based on observed outcomes in the prior patients used in the correlation of similarities. Additionally, or alternatively, the presented treatment options may include treatment details including one or more of power, intensity, dosage, duration, number of cycles, treatment regimen, co-treatments, and timing of each.

BRIEF DESCRIPTION OF THE DRAWINGS

Various aspects of the present disclosure are described hereinbelow with reference to the drawings, wherein.

DETAILED DESCRIPTION

The present disclosure is directed to an integrated approach for target biopsy, cytopathology, gene profiling or gene mapping, target treatment, outcome tracking, biologically targeted therapy, immunotherapy, external or internal radiation therapies, or any combinations thereof. One embodiment of the present disclosure is directed to aggregating data from large numbers of biopsies including data relating to each biopsy's cytopathology and its genetic profile. Re-biopsy data in which a second, third, etc., biopsy is taken of the same target at different times to assess changes in pathology, genetic profile, and other characteristic data is also collected. Treatment data is also collected and correlated to the biopsy data in instances where treatment is undertaken. The treatment data may include the manner of treatment (e.g., chemotherapy, ablation, resection, biologically targeted therapy, immunotherapy, external or internal radiation therapies, etc.) as well as more specific data such as duration and power levels of ablation, dosages of chemotherapeutic drugs, drug combinations, combined surgical and drug treatments, etc. Further, outcomes are monitored, both positive and negative, as a result of the treatment. As this data is collected and a greater number of genetic profiles are identified and associated with treatments and patient outcomes, predictive models are developed which can provide a clinician with a variety of treatment options tailored to the specific individual expressing a particular type of genetic profile in their particular tumor at a particular time in the progression of their disease.

Figure 1:
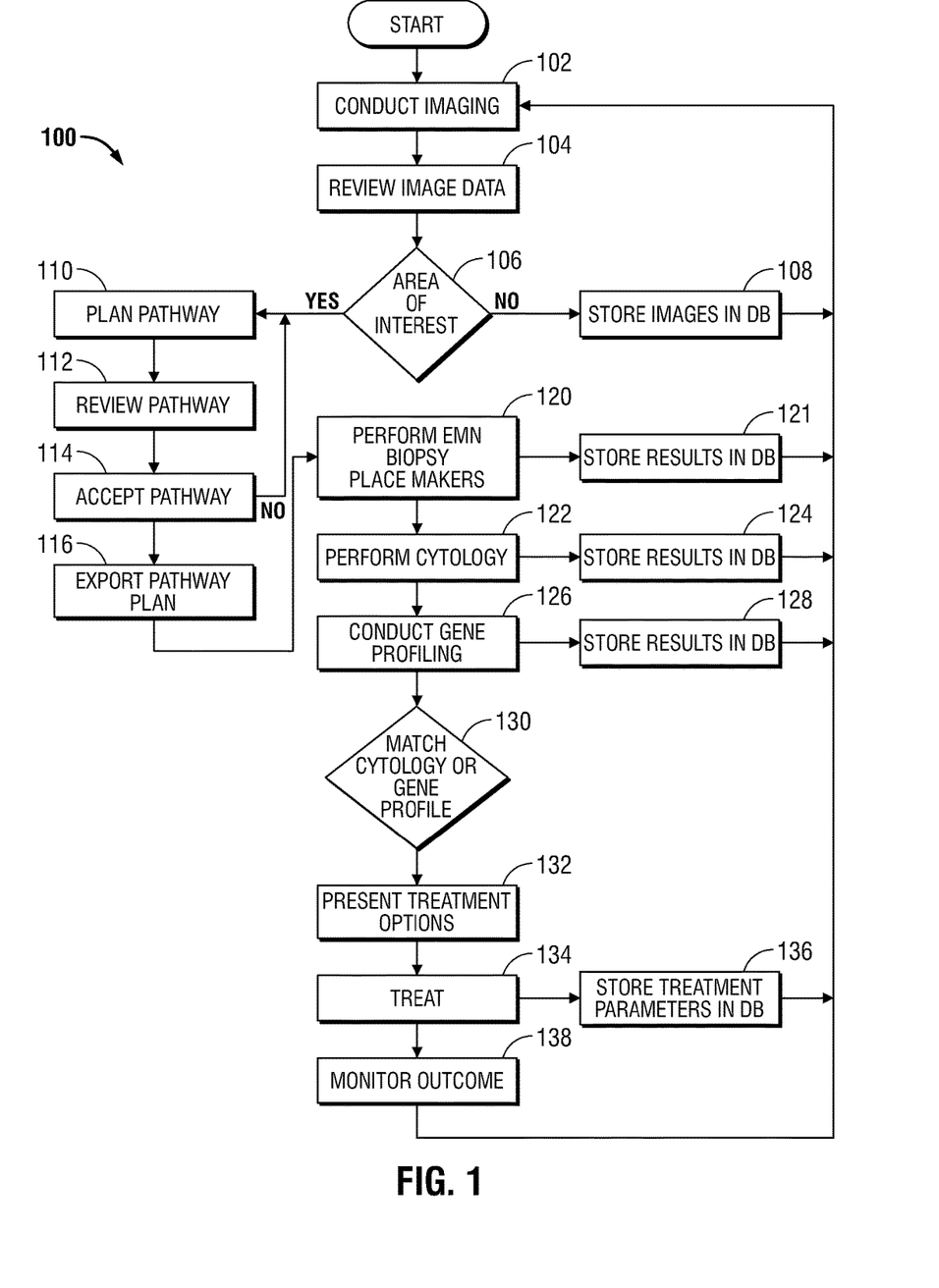
FIG. 1 is a flowchart depicting a method in accordance with the present disclosure.

One embodiment of the present disclosure is depicted in FIG. 1 which shows a method 100 for assessing and treating a patient and for collecting data to enable correlation of treatment with disease and generate predictive outcomes for a particular patient. At step 102, imaging is conducted of the patient, for example, Computer Tomography (CT) imaging, Magnetic Resonance imaging (MRI), fluoroscopy, x-ray or other imaging modalities. Other imaging modalities may be employed without departing from the scope of the present disclosure.

Once the images, for example CT images, have been generated, they may be imported into a pathway planning system 200 (FIG. 2) as described in co-pending and commonly assigned U.S. patent application Ser. No. 13/838,805 entitled PATHWAY PLANNING SYSTEM AND METHOD, the entire contents of which are incorporated herein by reference. The pathway planning system 200 may be embodied on a laptop, desktop, tablet, or other similar device, having a display 202, memory 204, one or more processors 206 and/or other components of the type typically found in a computing device. The pathway planning system may also be part of a thin client distributed network system wherein the data is stored remotely in memory 204 located on one or more servers, for example in the cloud, the software being executed by the processors 206 is stored and executed remotely on the one or more servers, and the display 202 and a user input such as a keyboard or mouse are the primary local components. As will be understood by those of skill in the art some local processing will also be necessary to receive, transmit, and manipulate data, for example for the display 202. Display 202 may be touch sensitive and/or voice activated, enabling display 202 to serve as both an input and output device. Alternatively, a keyboard (not shown), mouse (not shown), or other data input devices may be employed.

Figure 2:
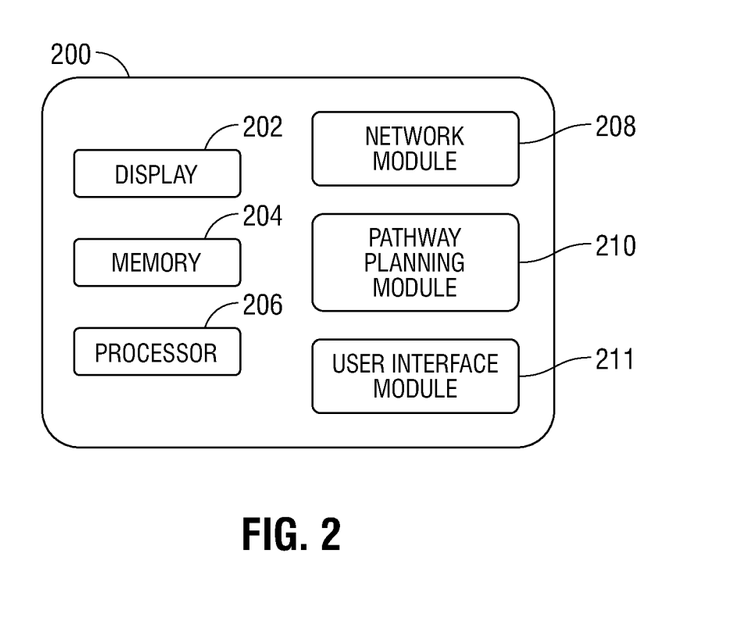
FIG. 2 is a schematic of a pathway planning device in accordance with the present disclosure.

Memory 204 may be any non-transitory, computer-readable storage media for storing data and/or software that is executable by processor 206 and which controls the operation of the pathway planning system 200. Pathway planning system 200 may also include a network module 208 connected to a distributed network or the internet via a wired or wireless connection for the transmission and reception of data to and from other sources. For example, computing device 200 may receive computed tomographic (CT) images of a patient from a server, for example, a hospital server, internet server, or other similar servers, for use during pathway planning. Patient CT images may also be provided to pathway planning system 200 via a removable memory e.g., a USB drive (not shown).

A pathway planning module 210 includes a software program stored in memory 204 and executed by processor 206 of the pathway planning system 200. As described in greater detail in the incorporated U.S. patent application Ser. No. 13/838,805, pathway planning module 210 guides a clinician through a series of steps to develop a pathway plan for later use during a medical procedure. Pathway planning module 210 communicates with a user interface module 211 displaying visual interactive features to a clinician on the display 202 and for receiving clinician input.

Using the tools of a pathway planning system 200, and particularly the pathway planning module 210, images, such as CT images, can be retrieved from memory 204 and reviewed on display 202 by a clinician at step 104. During review, if an area of interest is identified (step 106) this area of interest can be marked electronically in the image data and identified as a target. Either after identifying a target, or following complete review of all the image data and identification of all the targets, the method 100 can proceed to step 110 where a pathway plan from the area(s) of interest to a natural body opening, or a surgical body exit point (e.g., an incision) can be generated and stored in a database 500 (shown in FIG. 5) and associated with the patient.

Figure 4:
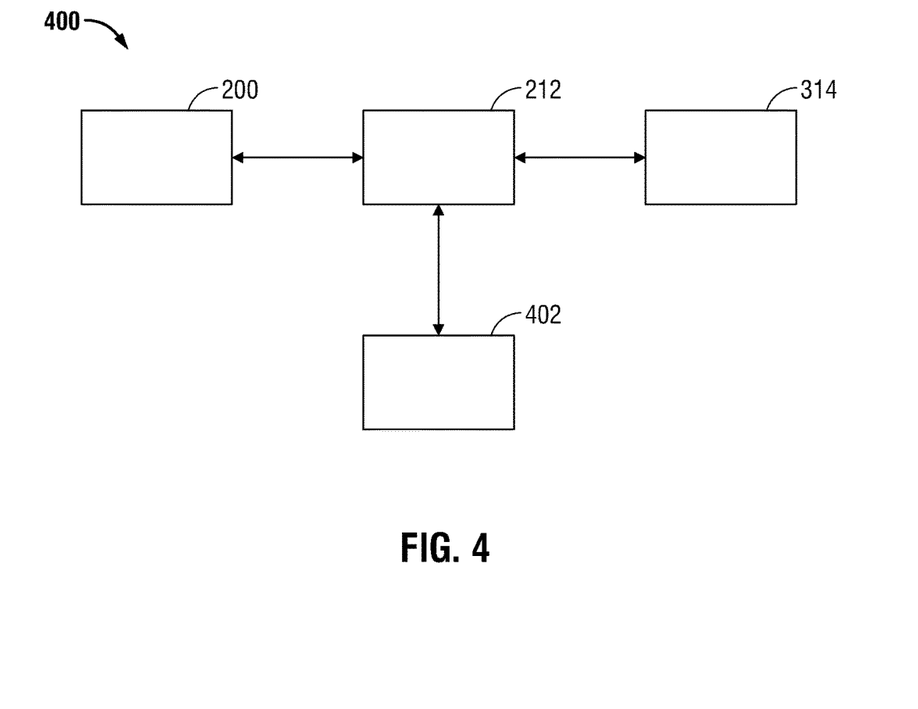
FIG. 4 is a computer network in accordance with the present disclosure.
Figure 5:
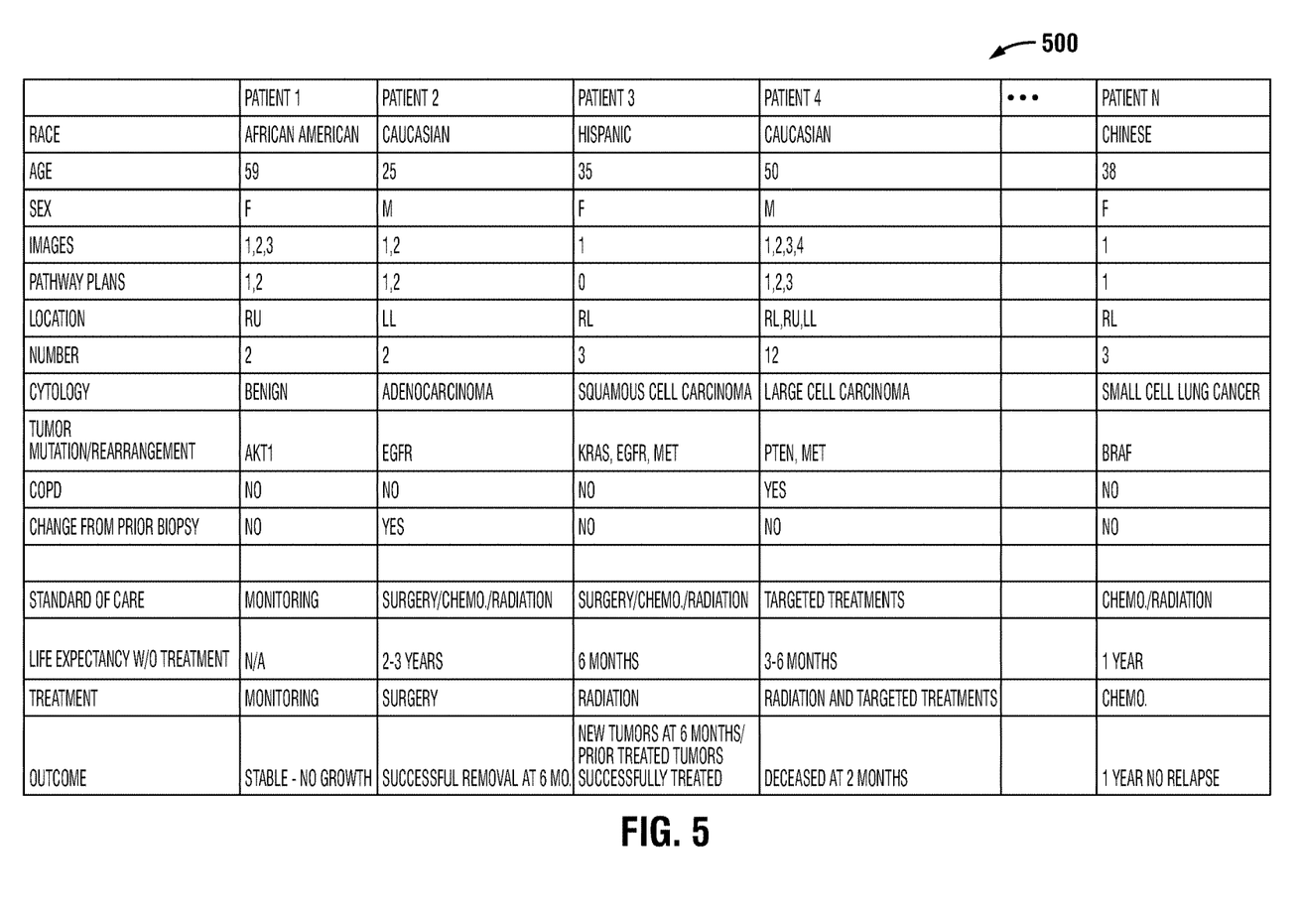
FIG. 5 is a sample database in accordance with the present disclosure.

If no areas of interest are identified in step 106, the image data collected in step 102 may be stored in a database 500, if not already stored therein, at step 108 and associated with the patient for comparison to later image data acquired of the same patient in order to assess changes in the patient over time. The database 500 may be stored locally on the pathway planning system 200 or remotely on a server 212 which is accessible via the network module 208, as shown in FIG. 4. As will be described in greater detail below, the image data as well as other relevant data of the patient are made available via database 500 for research and analysis by other clinicians for assessing their own patient's disease and treatment options. For example, some or all of the data stored in database 500 may be openly accessible for other physicians, clinicians, or researchers to access to assist in global treatment decision support.

Imaging and review steps 102 and 104 may be undertaken as part of an outcome monitoring step 138, described below. As a result, the imaging undertaken in step 102 may be undertaken and compared in review step 104 with prior imaging stored in the database 500 to determine whether prior treatments were successful, whether prior determinations of proceeding with "watchful waiting" are no longer appropriate, whether the disease has changed in some observable way (e.g., increased in size), and/or other changes in patient and disease state known to those of skill in the art and relevant to the observation, management and treatment of the disease.

Following generation of a pathway plan in step 110, the pathway plan can be reviewed by the clinician in step 112 and must be accepted by the clinician at step 114. If the pathway is not acceptable, the clinician can reject the plan and the pathway planning module 210 returns to step 108. The clinician can then utilize the tools of the pathway planning module 210 to generate a new pathway, or alter the existing pathway to a more desirable route. Once the pathway plan has been accepted in step 114 the pathway plan is stored in memory 204 and is ready for export for use in an Electromagnetic Navigation System 300 (EMN) depicted in FIG. 3. The pathway plan may be exported to the EMN system 300 using a portable memory such as a USB drive, or the memory 204 may be located on the server 212 as shown in FIG. 4 and accessible to both the pathway planning system 200 and the EMN system 300.

Figure 3:
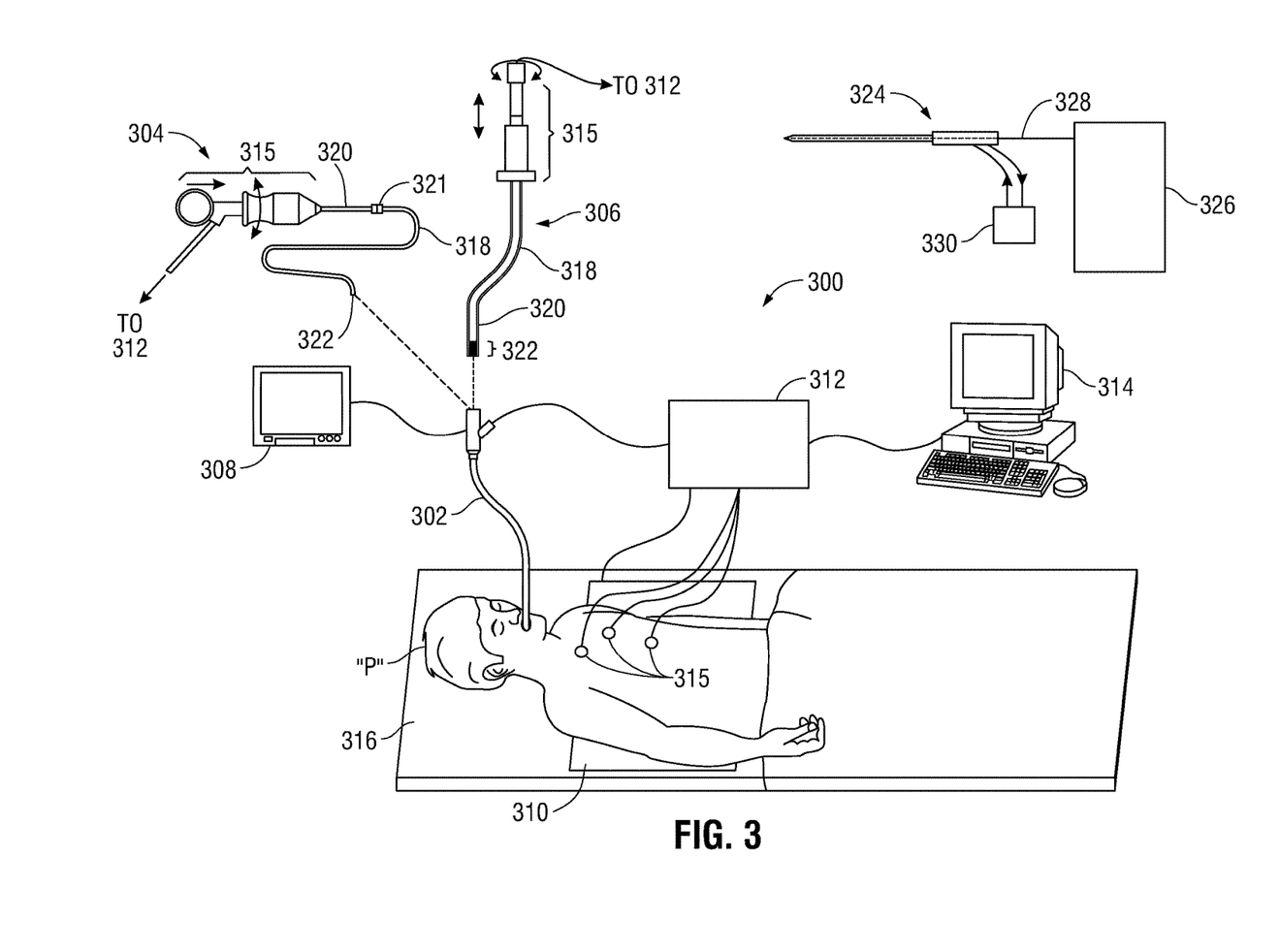
FIG. 3 is an Electromagnetic Navigation system in accordance with the present disclosure.

EMN system 300 may be the ELECTROMAGNETIC NAVIGATION BRONCHOSCOPY® system currently sold by Covidien LP. Typically the EMN system 300 includes a bronchoscope 302, one or more of two different types of catheter guide assemblies 304 and 306, monitoring equipment 308, an electromagnetic field generator 310, a tracking module 312, and a computer system 314. FIG. 3 shows a patient "P" lying on an operating table 316 including an electromagnetic field generator 310. Placed on the patient "P" are a number of sensors 315, whose position in the magnetic field generated by the electromagnetic field generator 310 can be determined by the tracking module 312.

Each of the catheter guide assemblies 304, 306 includes an extended working channel 318 that is configured to receive a locatable guide catheter 320 which includes a sensor 322. The locatable guide catheter 320 is electrically connected to the EMN system 300, and particularly, the tracking module 312 enables navigation and tracking of the sensor 322 within a luminal network, such as the lungs of a the patient "P," to arrive at a designated target. The extended working channel (EWC) 318 is configured to receive instruments including the locatable guide catheter 320 and sensor 322, biopsy tools (not shown) and a microwave ablation catheter 324, as well as others without departing from the scope of the present disclosure. A locking mechanism 321 ensures that the locatable guide catheter 320 and the extended working channel 318 move in concert. Each catheter guide assembly 304, 306 includes a handle 315 to enable movement and navigation through a luminal network such as the lungs of a patient "P."

As shown in FIG. 3, the microwave ablation catheter 324 is electrically connected to a microwave generator 326 via a feedline 328. The generator 326 supplies microwave energy to the catheter to treat tumors and lesions within the patient "P." A cooling circuit 330 cools the microwave ablation catheter 324 as is commonly known in the art to prevent damage to equipment and the patient except in those locations to be treated.

Stored on or accessible from the computer system 314 is navigation software enabling the navigation of one or more tools into the patient P following the pathway plan developed in steps 110-114. One such navigation software is described in detail in U.S. Provisional Patent Application No. 62/020,240 filed Jul. 2, 2014 by Brown, et al. and entitled SYSTEM AND METHOD FOR NAVIGATING WITHIN THE LUNG, the entire contents of which are incorporated herein by reference.

As described in the '240 Application, the sensor 322 detects a magnetic field generated by the electromagnetic field generator 310, and the tracking module 312 is able to identify the sensor's location within the magnetic field. The patient's location within the magnetic field, and particularly those portions of the patient which were previously imaged, are registered with the previously acquired images and the pathway plan imported to computer system 314. As a result, the navigation software stored on or accessible from the computer system 314 is capable of depicting a representation of the location of the sensor 322 within the patient P. This representative location may be in reference to rendered CT images or in reference to a 3D model generated from the CT image data or other types of images as described in the '240 Application.

Once the pathway plan is imported to the EMN system, and particularly computer system 314, a clinician is able perform EMN in step 120 to follow the pathway plan by manipulating the catheter guide assembly 304, 306, through the bronchoscope 302. The location of the sensor 322 within the patient "P" is depicted to the clinician on the images and/or 3D model of the luminal network of the patient, and the pathway to the target is shown in the user interface of the computer system 314. The clinician is able to manipulate the catheter guide assembly 304, 306 until the sensor 322 is proximate the target identified in step 106.

In embodiments involving re-biopsy (i.e., re-evaluating a target that has been previously been biopsied) it is possible to follow the same pathway plan used to access the target initially. However, given the relatively small cost of imaging, it is contemplated that typically clinicians will undergo a new imaging process 102 and pathway planning steps 110-116, each time a biopsy is contemplated. Changes to the target over time (either with or without treatment) and the need to confirm navigation to the appropriate location in view of these changes may necessitate a new imaging process 102 be undertaken.

Having arrived at the target location, the clinician can remove the locatable guide catheter 320 from the extended working channel 318. This may not be necessary if the sensor 322 is located on the extended working channel, as is also contemplated by the present disclosure. Regardless, having arrived at the target, as part of step 120, one or more biopsy samples will be taken of the target. The location from which the samples were taken may be electronically recorded in a navigation file as part of step 121. A navigation file is a computer record which may include both the pathway plan and the actual navigation steps taken during the EMN. A graphic representation of the biopsy (e.g., an electronic marker) may be placed by in the navigation file, and displayed to the clinician on the user interface of the computer system 314. In addition to a graphic representation of the biopsy, an electronic marker may include annotations denoting specific biological data such as, for example, tumor type and subtype, cytology and histology test results data, genomic/proteomic data, resistance data, etc. Additionally, the annotations may co-note anatomical details including, for example, distance to airway, fissure, vascularity, etc.

In addition to electronic markers, physical fiducial markers may be placed at or near each of the biopsy sites. These markers ease finding the target in future CT scans and other imaging techniques and make it easier to revisit the target at a later date in a subsequent EMN procedure and for performing re-biopsy as may be necessary in the outcome monitoring steps described below.

After taking a biopsy at a target and placing markers at the target, the clinician returns to the pathway plan. Following reinsertion of the locatable guide catheter 320 with sensor 322 the clinician proceeds to navigate to the next target. Again samples are taken of this and every target until all the targets have been navigated to, electronically marked, biopsies taken and physical markers placed at the targets. As noted above, in instances where the EWC 318 includes sensor 322, reinsertion of the locatable guide catheter 320 is unnecessary.

With each biopsy, cytopathology must be undertaken at step 122 to determine the disease state of the cells recovered from the target in the biopsy. The results of the cytopathology have at least two uses. First the results of cytopathology identify whether the individual patient has cancer and the type of cancer; another disease, or whether the target is a benign growth. Second, each biopsy represents a data point to be incorporated into a potential treatment database 500 and predictive outcome models generated from the database 500, as will be described in greater detail below.

Cytopathology may be performed using a rapid on-site evaluation ("ROSE") for immediate testing. Thus, in some instances the testing may be performed even before the clinician moves on to the next target following the extraction of a biopsy. In some instances, this ensures that sufficient samples are taken from each target for the biopsy, allowing the clinician to repeat the biopsy immediately, if needed. In addition, in some instances, use of ROSE procedures enables the clinician to perform immediate treatment of the target without the need for a subsequent EMN, thus streamlining the treatment process and reducing the number of procedures and time between procedures for the patient. The results of cytopathology are stored in a database 500, shown in FIG. 5, in step 124. This data is available to the clinician for treatment and monitoring of the specific patient "P," as well as for use in comparison to other patients to identify treatment options and predicting outcomes, as will be described in greater detail below. Additionally the cytopathology may be part of a point of care, (e.g., bedside sequencing system) enabling even faster analysis of biopsy samples and interconnectivity with the systems and methods described herein.

Cytopathology may be part of the continuum of care as part of an outcome monitoring step 138 described below. As a result, the cytopathology may be taken and compared with prior cytopathological results to determine whether prior treatments were successful, whether prior determinations of proceeding with "watchful waiting" is no longer appropriate, whether the disease state has advanced from the last cytopathological testing or whether the disease has become resistant to the prior treatments, as well as other determinations.

With the cytopathology undertaken at step 122, either serially (as shown) or in parallel, genetic testing can be undertaken in step 126. The genetic testing may reveal a gene profile or gene mapping of the biopsy samples, or other information. The gene profile or gene mapping may express a mutation of a gene, for example the biopsy in question may be positive for mutations in the epidermal growth factor receptor (EGFR), anaplastic lymphoma kinase (ALK) mutations, and Kirsten rat sarcoma (KRAS) and other rat sarcoma (RAS) family member mutations, as well as other genetic markers known to those of skill in the art. Each of these mutations, as well as other genetic makers, is associated with and has been observed in a variety of cancers. The gene profiling or gene mapping is conducted in step 126, and the data is stored in database 500 in step 128. In step 126, genetic testing is undertaken for each target identified in the pathway planning step 110-114 as different targets may express different or no mutations despite occurring in the same patient. As will be recognized by those of skill in the art, genetic profiling of the type contemplated here requires use of specialized laboratory facilities and may require some time to perform. As such, there may be a delay between the steps of performing the biopsy in step 120, conducting cytopathology and gene profiling in steps 122 and 126, and the subsequent steps of the method 100. Current technology enables results to be processed in as fast as 24 hours, but it is contemplated that as technology develops real-time gene profiling will be developed enabling a real-time on site gene profiling, and further streamlining the process of identification and treatment of the disease.

As with imaging and cytopathology, genetic mapping of a biopsy sample may be part of the continuum of care as part of an outcome monitoring step 138 described below. As a result, the genetic map may be taken and compared with prior genetic maps to determine whether prior treatments were successful, whether prior determinations of proceeding with "watchful waiting" is no longer appropriate, or whether the disease has further mutated in some fashion. Again, each of these genetic mappings is stored in the database 500.

Genetic mapping data may not be solely limited to genetic mapping to particular locations of cancer (e.g., lung, liver, stomach, etc.). Rather, if available, database 500 may include data for a variety cancers, many of which are completely unrelated to the individual patient "P." While not typically considered for treatment, where a tumor in the lung of patient "P," for example, expresses the same mutation as one take from a different patient's liver that data may prove useful in determining the treatment options for the patient "P." As a result, the treatment of patient "P," as will be discussed below may bear a closer resemblance to a liver cancer treatment protocol than a typical lung cancer treatment protocol. For example, if microwave ablation is the desired treatment regimen, the power and duration settings for the ablation may be more closely associated with the liver cancer treatment settings in view of this genetic mapping, where that type of treatment has proven effective in the treatment of liver cancer. Other correlations of data from genetic profiles and cytopathology from a specific biopsy sample are enabled by the collection and cross-referencing of the data in database 500.

In step 130, the clinician may employ the computer system 314 to access the database 500, which may be stored either locally or on server 212, to compare the patient "P" data with other individuals who have been previously treated. Alternatively, the clinician may use any computing device 402 capable of accessing the network 400, and specifically the server 212 as shown in FIG. 4. This enables the clinician to conduct the EMN, collect the biopsy samples, have cytopathology and genetic testing performed, and subsequently review the aggregated results for that patient "P" at a later date. The computing device 402 may be a laptop, tablet, smart phone, desk top computer, or any other network enabled device.

By cross referencing genetic profile or gene mapping with cytopathological information relating to the existence of cancer, and more importantly a specific type of cancer, and further with data such as age, sex, race, location of the cancer, medical history of the patient, specified standard of care, type of treatment undertaken, and observation of the outcomes the fields of database 500 can be filled with actual data from an ever increasing population of patients. This data is then accessible to clinicians when treating specific patients as well as for further analyses in order to determine correlations between the data, identify potential outcomes of different treatments for groups and types of patients, and to develop revised protocols for the standard of care. Effectively, with enough patient data, greater and greater predictive capability can be made available to the clinician for use in determining the best course of action for the particular patient "P" seeking treatment.

Figure 6:
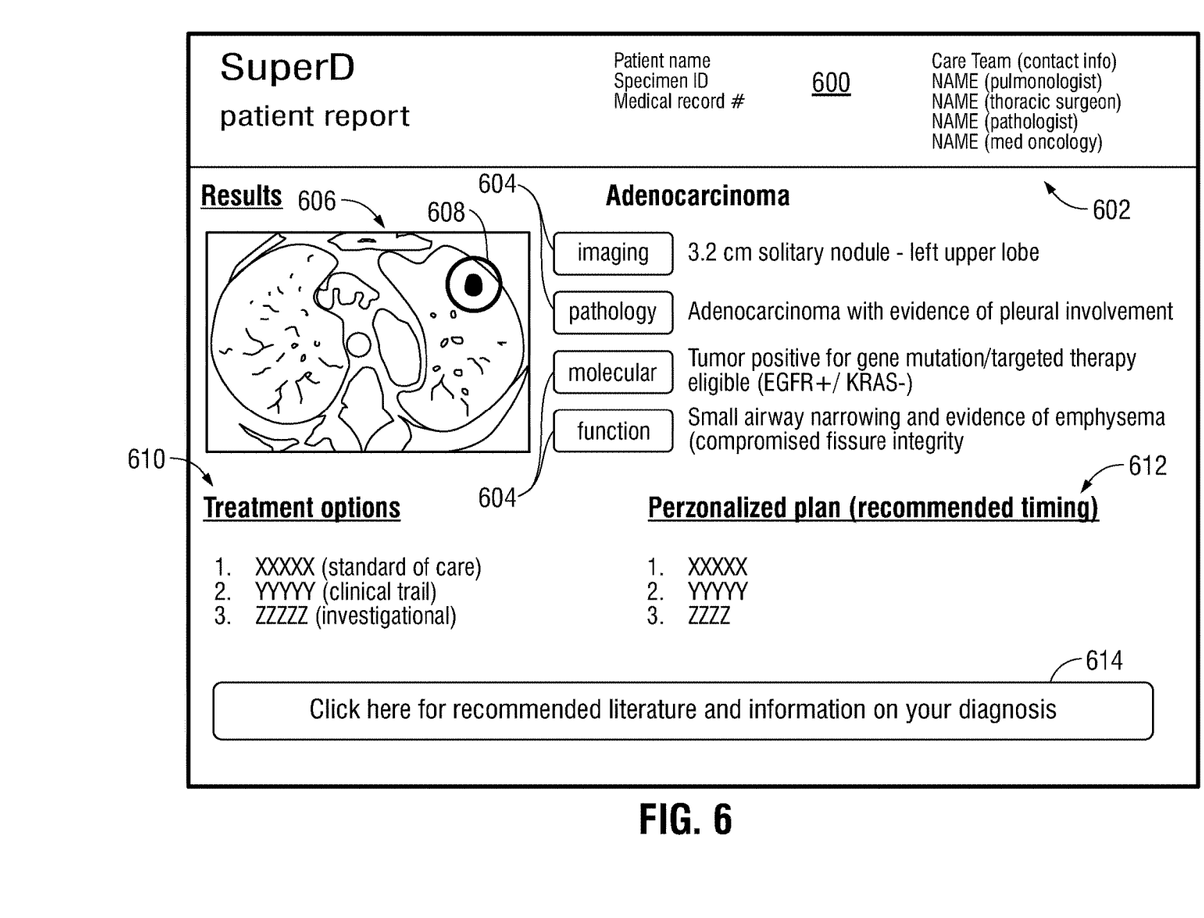
FIG. 6 is a sample web page in accordance with the present disclosure.

In one embodiment of the present disclosure, the server 212 is a web-server enabling access via the internet. Further, the web-server 212 runs software presenting a series of web pages to the clinician via the connection to computer system 314 or device 402, one such web-page is shown in FIG. 6. Other web pages presented via the software running on sever 212 may include those depicted in incorporated by reference U.S. Patent Provisional and Utility Application Nos. 62/020,240 and 13/838,805.

FIG. 6 is an exemplary web page 600 displaying in step 132 the result of the analysis step 130 determining the cytological and/or gene profile analogues for the patient "P." Web page 600 provides an analysis of the specific patient "P" data in comparison with that stored in database 500 of other patients whose samples have been collected and analyzed previously. Web page 600 identifies the patient name and medical record number of that patient as well as the identity of the care team for that patient "P." Web page 600 includes a number of fields which can be populated using a combination of data from the database 500 relating to the specific patient "P," data generated based on the comparison of the patient's data and the data of other patients having some level of similarity, and data retrieved from other databases.

On web page 600, a results banner 602 may be used to provide an overview of the diagnosis for a patient "P." As shown in FIG. 6, this overview is an identification of the type of cancer identified by the pathologist, for example an Adenocarcinoma. Below the results banner 602 are a series of fields of data relating to the patient "P." Each field has a tab 604 presenting one each for "imaging," "pathology," "molecular," and "function." Other tabs 604 may be presented without departing from the scope of the present disclosure. Next to each of these tabs is a summary of the contents to be found in the database 500 for the patient "P" related to each tab 604. For imaging, the size and location of the target are identified. For pathology the type of cancer and other information from the cytopathology are presented. Next to the tab 604 labeled molecular are the results of the genetic profiling or testing, e.g., the identification of a mutation. Next to the tab labeled function is an assessment of other factors relating in this example to lung function of the patient "P." Other tabs may include an assessment of the patient's ability to withstand the rigors of treatment options (e.g., chemotherapy, radiation, and/or surgery), as well as other data about the patient.

A further field 606 depicts a representative image of the target 608 to be treated. By clicking on the image or on the neighboring imaging button 604, the web-page 600 may reveal a new window or web page displaying the CT image data or present the image data in the form as seen in the pathway planning module 210. This review of the CT image data enables the clinician to orient themselves with respect to the target and confirm information about the target 608. Similarly, by clicking or selecting any of the buttons 604, the clinician may be presented with a new web-page including detailed information from the database 500 for the individual patient "P."

Field 610 in FIG. 6 presents treatment options that are available for the patient "P." These treatment options may include the "standard of care," which is typically considered the treatments that are accepted by medical experts as a proper treatment for a certain type of disease and that are widely used by healthcare professionals. This is also called best practice, standard medical care, and standard therapy. The standard of care may be set by, for example, the National Cancer Institute at the National Institutes of Health or by a local or regional governing body for a particular practice of medicine. The standard of care for a particular cancer will depend on size, location, and dispersion and may include resection, lobectomies, radiation, radiosurgery, chemotherapy, targeted therapies, photodynamic therapy, electrocautery, biologically targeted therapy, immunotherapy, external or internal radiation therapies, and others as well as ordered combinations of these treatments.

While the standard of care for a particular disease is the recommended course of action, clinicians will immediately recognize that there may be reasons not to follow the standard of care. For example, if the standard of care for a particular disease is surgery, but the patient is old and infirm and might be incredibly stressed by the surgery, a clinician in consultation with the patient may decide the standard is not appropriate for that particular patient. To assist in these instances, field 610 may also identify whether there are existing "clinical trials" on-going which may be of interest to the clinician and in which the patient may wish to participate in order to receive developmental treatments. These clinical trials can be very important to patients, particularly if it is deemed that the standard of care has not been effective or is otherwise undesirable. A further option is the availability of investigational treatments, for example, through the U.S. Food and Drug Administration's Expanded Access (compassionate use) programs. These are typically the same therapies available to the patient via the clinical trials, but do not require participation in the trial, and do not run the risk of receiving the placebo that is common for a portion of the trail members. Selecting on the web page 600 one of the specified treatment options in field 610 will provide the clinician with more information regarding the details of that option.

Some of the details of the treatment options available to the clinician using the system described herein are only available as a result of the collection, cross-referencing and sorting of the data in the database 500. As a result of the previously collected data, including data relating to the selected treatment for patients as well as the observed outcomes, described in greater detail below, which is collected, stored, and cross referenced in database 500, a clinician is given ever more granular data to compare to the patient "P" and provide diagnosis and prognosis information. The increased granularity or particularity of information including the cytopathology, gene profiling, treatment options and observed treatment outcomes allow the clinician and the patient to develop the personalized plan for treatment depicted in FIG. 6 as filed 612. A further field depicted on web page 600 is the personalized plan 612. This personalized plan displays the course of action that is decided upon in consultation with the patient "P," and the care team on how to treat the particular patient after considering all of the information described hereinabove.

As will be appreciated by those of skill in the art, data in the database 500 (including imaging, navigation, biopsy, genetic, etc.) may be stored individually, and/or annotated as composite report together, including overlaid on imaging data set. In addition, follow-up biopsies, and the data associated with them, may be overlaid by time course for longitudinal studies (seeing results/outcomes over time); one patient or aggregated patient pools. The data in the database 500 may be used to develop new clinical trials. In at least one embodiment of the present disclosure the data in the database 500 may be presented in an open source format for other physicians or clinicians to access and inform a broader body of clinicians on treatment options, decisions, and predictive outcomes.

In one embodiment the personalized plan, and the recommended series of actions depicted in field 612 are generated by software running on the server 212. In such a scenario, the software compares the data in database 500 and identifies a sufficient number of analogues for the patient "P" based on all of the available data. The identified analogues' treatment options are then compiled and those with an occurrence interval above a predetermined threshold may be selected by the software. Alternatively, a selected number of the most commonly applied treatments may be selected by the software. In another alternative, all selected treatments are ranked based on the observed patient outcome, and those with the best outcome are presented to the clinician. Still further, where a treatment regimen of multiple different treatments are identified these too are presented to the clinician in the personalized plan 612. Further, for each treatment option, specific details of frequency, power, duration, dosage, co-treatment options, and others may be presented to enable the selection of a very detailed treatment plan to best treat the patient "P," based on the data recorded in database 500 of prior treatments having the most successful outcomes for patients with the most similar diseases, disease states, and other correlated data between the patient "P" and the prior patients' data stored in database 500.

Additionally, sorting or ranking of treatment options may also be based on specific tumor type and subtypes, genetic mapping of tumor and other non-cancerous tissue, by disease stage and location, by similar pooled patient's including data such as race, ethnicity, age, family history, reported treatment outcomes by specific treatment type, outcomes including overall progression free survival, overall survival, time to recurrence and/or resistance, and type of resistance (mutation type). Further, data may also be sorted in reverse, where data is filtered based on gene mutations, treatments and outcomes. In such cases, the output is determining who response best (which age group, race group, ethnic group, family history group, etc.), and of which whole genome sequencing is conducted (on non-tumorous tissue) to identify cancer and non-cancer related genes to help understand prognosis/disease mechanisms.

As a further alternative, the database 500 may be searchable directly by the clinician, enabling them to make their own assessments, either with or without software parameter limitations. For example, the clinician may perform a search using a form (not shown) where the clinician inputs or selects the data which is determined most important. In one instance this may be pathology, gene profile, and age of the patient. The results of this simple inquiry will enable the clinician to review both the treatments and outcomes for similarly aged individuals having the same cytological and/or gene profile as the patient "P." With this data the clinician and the care team can make assessments of how best to proceed for patient "P." Alternatively, the software may consider the inquiry and simply report back the ranked treatment options and expected treatment outcome for each based on the inquiry. As will be appreciated, the greater the degree of similarity between prior patients and the current patient "P," the greater the confidence that a treatment with a successful outcome can be repeated in patient "P." Thus, the ability for the clinician to consider the recommendations of the software and then look at the underlying data and make additional comparisons may be very useful. The software enables the entire file of the prior patients identified as analogues to be reviewed by the clinician to consider whether an identified analogue should be included or excluded from the group used to develop the personalized plan. As will be appreciated, the data in database 500 that is searchable by clinicians, with the exception of patient data for those patients under the care of a particular physician will be scrubbed of identification data and incapable of revealing information in conflict with privacy protection rules.

Web page 600 in FIG. 6 also includes a tab 614 connecting the clinician to literature and other information that might be relevant to the clinician in assessing the diagnosis and developing the personalized plan 612. This might include treatment protocols, potential side effects of a particular treatment, and others. This data may be resident in database 500 or the software operating on server 212 may direct the clinician to an appropriate location where the information is accessible, for example the website for the National Institute of Health (U.S.) or the National Health Service (U.K.), or other relevant repositories of such information.

Following review of all the available data described above in connection with step 132 and web page 600, the care team decides on a particular treatment plan, as embodied in field 612, which is stored in database 500, and then effectuated. Treatment occurs in step 134.

In one example, microwave ablation catheter 324 is inserted into EWC 318, and into the target and microwave ablation energy is applied to treat the target. A variety of power settings, durations, cycle information, and other treatment options may be employed to most effectively treat the tumor without unnecessarily affecting adjacent tissue. In addition a variety of co-treatment options may be followed including, following the ablation with chemotherapy, radiation, or other therapies. The occurrence of the treatment 134 is recorded into database 500, including any relevant factors relating to the treatment. For example, if it is determined that the treatment is to be via microwave ablation, other factors might include power, duration, number of cycles of treatment, number of sites treated, etc. Similarly, if the treatment is via surgery additional factors included might be approach to site (anterior or posterior), duration of surgery, etc. Or if a combination of treatments, the type of drug therapy and dosage and the relevant radiation parameters. Again these data are recorded in database 500 for inclusion both in the record of the individual patient "P" and for comparison and use in developing a treatment plan for subsequent patients.

Following treatment 134, and storing the treatment data to the database 500 at step 136, a patient will typically have a regimented follow-up review with their doctor to observe the effectiveness of the treatment allowing for outcome monitoring 138 to be conducted. This may include imaging of the target that was treated. These images will be stored in database 500 to make them available to both the care team for the patient "P," as well as allowing the effectiveness of a treatment to be considered by other clinicians when making treatment decisions for their patients, as described above with respect to step 132. The images taken as part of the follow-up observations may be stored in database 500 along with other observations of the treatment by the clinician including challenges for the patient such as nausea, weakness, hair loss, etc., so that all of this empirical data of the treatments can be made available and considered by these other patients and their physicians.

These outcome monitoring steps 138 may be separate from, or may be part of, steps 102-106, when a patient undergoes these steps for the second and subsequent times. The result is a continuum of care for a patient, where their specific treatment is personalized for them and based on the widest possible knowledge that affects them specifically and their cancer specifically, but further is made available for other patients and clinicians to consider in their treatment of other patients.

A further benefit of this continuum of treatment is the gathering of statistical data relating to the frequency and timing of mutations of lesions. Each time either cytopathology or a gene profile test is conducted an additional data point for the disease in question is captured. This data can be aggregated in the database to determine if there is any regularity to the changes and mutations of the disease. Further, likelihood of mutation can be assessed in view of the additional data. For example, it may be determined that a mass discovered in a geriatric patient, even if left untreated, will not significantly mutate or change into a more deadly form that would significantly impact the life expectancy of the patient, whereas the same mass expressing the same genetic and cytological profile in a child can be expected to mutate and progress rapidly and thus require a very different course of action.

Further, the data stored in database 500 may define correlations between an early detected mass and a late stage cancer which were heretofore unknown. This correlation allows for greater level of positive outcomes to be achieved by better defining those presentations that require immediate aggressive treatment, even if currently benign, as compared to those presentations that can accept a more graduated treatment regimen without an increased likelihood of mortality.

Described herein are a few options for retrieving samples of a target and treating the disease. The EMN system 300 is particularly useful for biopsy sampling via biopsy needles or forceps. In addition, the use of the EMN system 300 for microwave ablation of the target using a flexible microwave catheter 324 as depicted in FIG. 3 is also contemplated. However, other known techniques are also contemplated within the scope of the present disclosure for both data generation and treatment. For example, it is known that tumorous tissue generally has a different cellular structure and composition than surrounding tissue. As a result, tumors and lesions exhibit a different spectroscopic response than healthy tissue, that is, the tumorous tissue emits energy differently than the surrounding tissue. As a result, this difference in spectroscopic response can be measured and used to provide greater clarity with respect to the location, meets and bounds of the tumor, and guarantee of placement. In this respect the tumor or lesion has a spectroscopic fingerprint which can be used to distinguish the tumor or lesion from surrounding tissue. Accordingly, one embodiment of the present disclosure employs the use of an electromagnetic signal emitter (e.g., microwave, infrared, etc.) emitting a signal at a non-treatment level. The tumor or lesion will absorb the signal (as will the healthy tissue) but the tumor or lesion will emit a very different response to this energy than the healthy tissue. This difference in response (e.g., the emittance of absorbed energy) can be measured using a receiver (e.g., a microwave antenna or a fiber optic strand) and the received signal analyzed to distinguish tissue. This received signal of emittance can then be saved in the database 500 for yet another data point regarding that tumor which may be useful in follow-up procedures for the specific patient as well as for comparative purposes for other patients' diseases. In one aspect of the present disclosure this "spectroscopic fingerprint" can be used to provide either guidance to cytopathologists or as a confirmation of the cytopathological results. Further, as greater data is collected and the confidence interval of spectroscopic fingerprints increases, a clinician may have sufficient confidence in such data that treatment may be commenced based on this data even prior to receiving the cytopathological and genetic testing results.

Yet a further embodiment of the present disclosure relates to the use of markers. As described above, fiducial markers, both real and virtual, can be placed in the patient or the image data file during use of the EMN system 300. However, a variety of other types of markers may also be employed without departing from the scope of the present disclosure. For example, following genetic testing, it may be determined that the desired course of action is a "watchful waiting" approach. In such a scenario it can be desirable to isolate, to the extent possible, the tumor from the healthy tissue. One method of achieving this is to employ a cross-linking agent which has a particular affinity to a particular gene mutation. These materials can be injected into the tumor via the biopsy needle, and over time will cross-link to essentially harden the mass or tumor. This may be beneficial to enable palpation of the tumor, or to increase its visibility. In one aspect of the present disclosure, the cross-linking agent has a coloring agent associated with it, for example, a fluoroscopic dye or an autofluorescent dye. These techniques also make the tumor or mass easier to find in subsequent EMN procedures and enable visualization of the tumor. Other materials that may be utilized to isolate the tumor from surrounding tissue and make it easier to identify include magnetic particles compositions which stain the tumor.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

The invention claimed is:

1. A user interface for assessing a target and presenting treatment options, the user interface comprising:
 a present patient data field;
 a care team field;
 a disease identification field;
 a plurality of fields presenting data including one or more of imaging data, cytopathological data, genetic information and treatment options for an identified target of a present patient, wherein the treatment options include power and duration parameters for an ablation treatment and are based on a correlation of similarities in data from a plurality of prior patients having been treated by an ablation treatment and the data for the identified target of the present patient; and a personalized plan field presenting a personalized treatment plan for the present patient, the personalized treatment plan selected by software based on one or more treatment options having a ranking exceeding a preconfigured threshold, the ranking based on an observed patient outcome of each treatment option of the one or more treatment options for the plurality of prior patients, the personalized treatment plan including personalized power and duration parameters for ablation treatment of the identified target of the present patient, wherein the personalized power and duration parameters are determined by identifying a match between a genetic mutation in the identified target of the present patient and a genetic mutation in a target of at least one patient of the plurality of prior patients.

2. The user interface of claim 1, wherein the correlation of similarities is based on cytopathological data stored in a database and the cytopathological data of the present patient.

3. The user interface of claim 1, wherein the correlation of similarities is based on the genetic information stored in a database and the genetic information of the present patient.

4. The user interface of claim 1, wherein the correlation of similarities is based on at least one of the imaging, cytopathology, genetic information, sex, race, and age data stored in a database and the corresponding data of the present patient.

5. The user interface of claim 1, wherein the presented imaging data of the target, cytopathology of the target, and genetic information of the target are selectable by a user to present further details of each.

6. The user interface of claim 1, wherein the treatment options include a standard of care.

7. The user interface of claim 1, wherein a clinician can select one or more of the presented treatment options to pursue to treat the present patient.

8. The user interface of claim 1, wherein the presented treatment options are those most commonly undertaken treatments administered to the prior patients having the same cytopathological expression as the present patient.

9. The user interface of claim 1, wherein the presented treatment options are those most commonly undertaken treatments administered to the prior patients having the same genetic information as the present patient.

10. The user interface of claim 1, wherein the presented treatment options include an expected outcome, the expected outcome based on observed outcomes in the prior patients used in the correlation of similarities.

11. The user interface of claim 1, wherein the presented treatment options include treatment details including one or more of power, intensity, dosage, duration, number of cycles, treatment regimen, co-treatments, and timing of each.

12. The user interface of claim 1, further comprising a diagnosis field.

13. The user interface of claim 12, further comprising a field presenting literature and other information relevant to the diagnosis.

14. The user interface of claim 1, further comprising a field presenting function data of the present patient.

15. The user interface of claim 14, wherein the function data provides details regarding a health of the present patient.

16. The user interface of claim 14, wherein the function data provide details on a health of an organ in which the target is located.

17. The user interface of claim 1, further comprising:
a rendering of the present patient's branched luminal network; and
a pathway plan for navigating a medical instrument through the patient's branched luminal network to the identified target.

18. The user interface of claim 17, further comprising a representation of the medical instrument in the rendering of the patient's branched luminal network corresponding to a tracked position of the medical instrument within the present patient's branched luminal network.

19. The user interface of claim 1, wherein the genetic mutation in the identified target of the present patient is the same as the genetic mutation in a target of at least one patient of the plurality of prior patients, and the personalized power and duration parameters for the present patient are generated by adjusting the treatment options for the identified target.

20. A user interface for assessing a target and presenting treatment options, the user interface comprising:
a plurality of fields presenting data including one or more of imaging data, cytopathological data, genetic information, and treatment options including power and duration parameters for ablation treatment of an identified target of a present patient, the power and duration parameters based on a correlation of similarities in data from a plurality of prior patients having been treated by an ablation treatment and the data for the identified target of the present patient; and
a personalized plan field presenting a personalized treatment plan for the present patient, the personalized treatment plan selected by software based on one or more personalized treatment options having a ranking exceeding a preconfigured threshold, the ranking based on an observed patient outcome of each personalized treatment option of the one or more personalized treatment options on the plurality of prior patients, the personalized treatment plan including personalized power and duration parameters for ablation treatment of the identified target of the present patient, wherein the personalized power and duration parameters are determined by:
identifying a match between a cytopathological profile of the identified target of the present patient and a cytopathological profile of a target of at least one patient of the plurality of prior patients having a same profile as the cytopathological profile of the identified target of the present patient; and
adjusting the treatment options of the identified target based on the identified match.

* * * * *